United States Patent
Xu et al.

(10) Patent No.: US 11,684,432 B2
(45) Date of Patent: Jun. 27, 2023

(54) STERILIZABLE FLEXIBLE SURGICAL INSTRUMENT SYSTEM

(71) Applicant: Beijing Surgerii Robotics Company Limited, Beijing (CN)

(72) Inventors: Kai Xu, Beijing (CN); Zhengchen Dai, Beijing (CN); Shu'an Zhang, Shanghai (CN); Jiangran Zhao, Beijing (CN); Zhixiong Yang, Beijing (CN); Huan Liu, Beijing (CN); Zenghui Liu, Beijing (CN)

(73) Assignee: Beijing Surgerii Robotics Company Limited, Beijing (CN)

( * ) Notice: Subject to any disclaimer, the term of this patent is extended or adjusted under 35 U.S.C. 154(b) by 1124 days.

(21) Appl. No.: 16/329,745

(22) PCT Filed: Aug. 31, 2017

(86) PCT No.: PCT/CN2017/099856
§ 371 (c)(1),
(2) Date: Feb. 28, 2019

(87) PCT Pub. No.: WO2018/041205
PCT Pub. Date: Mar. 8, 2018

(65) Prior Publication Data
US 2019/0231452 A1 Aug. 1, 2019

(30) Foreign Application Priority Data

Aug. 31, 2016 (CN) .......................... 201610796082.4
Aug. 31, 2016 (CN) .......................... 201610796089.6

(51) Int. Cl.
*A61B 34/30* (2016.01)
*A61B 34/00* (2016.01)
*A61B 17/00* (2006.01)

(52) U.S. Cl.
CPC .............. *A61B 34/30* (2016.02); *A61B 34/70* (2016.02); *A61B 2017/00477* (2013.01);
(Continued)

(58) Field of Classification Search
CPC .................... A61B 34/30; A61B 34/70; A61B 2017/00477; A61B 2034/301; A61B 2034/302; A61B 2034/305
See application file for complete search history.

(56) References Cited

U.S. PATENT DOCUMENTS

2011/0213383 A1   9/2011  Lee et al.
2011/0295242 A1*  12/2011 Spivey ................. A61B 17/068
                                                          606/1

(Continued)

FOREIGN PATENT DOCUMENTS

CN    103085083 A    5/2013
CN    103315781 A    9/2013

(Continued)

OTHER PUBLICATIONS

ISA State Intellectual Property Office of the People's Republic of China, International Search Report Issued in Application No. PCT/CN2017/099856, dated Dec. 1, 2017, WIPO, 4 pages.

(Continued)

*Primary Examiner* — Katherine M Shi
*Assistant Examiner* — Mikail A Mannan
(74) *Attorney, Agent, or Firm* — McCoy Russell LLP

(57) ABSTRACT

Disclosed is a sterilizable flexible surgical instrument system, comprising a flexible continuous body structure. The flexible continuous body structure comprises a distal structural body, a middle connecting body and a proximal structural body. The distal structural body comprises at least one distal structural segment, the distal structural segment comprising a distal spacing disk, a distal fixing disk and a (Continued)

structural backbone. The proximal structural body comprises the same number of proximal structural segments as distal structural segments, the proximal structural segments comprising a proximal spacing disk, a proximal fixing disk and a structural backbone. The proximal structural segment is linked to the distal structural segment via a middle connecting body. A transmission unit is further comprised. The transmission unit comprises a transmission mechanism fixing plate arranged in front of the middle connecting body. A gear transmission mechanism for converting a rotary motion input into a linear motion output is arranged on the transmission mechanism fixing plate. An output end of the gear transmission mechanism is securely connected to one end of a driving backbone via a adaptor, and the other end of the driving backbone passes through the proximal spacing disks, and is then securely connected to the proximal fixing disks.

18 Claims, 12 Drawing Sheets

(52) U.S. Cl.
CPC ... *A61B 2034/301* (2016.02); *A61B 2034/302* (2016.02); *A61B 2034/305* (2016.02)

(56) References Cited

U.S. PATENT DOCUMENTS

| | | | |
|---|---|---|---|
| 2015/0223832 A1* | 8/2015 | Swaney | A61B 34/10 |
| | | | 703/1 |
| 2016/0135914 A1* | 5/2016 | Isoda | A61B 34/72 |
| | | | 606/130 |

FOREIGN PATENT DOCUMENTS

| | | |
|---|---|---|
| CN | 103707322 A | 4/2014 |
| CN | 104546048 A | 4/2015 |
| CN | 106236270 A | 12/2016 |
| CN | 106344157 A | 1/2017 |
| EP | 2008594 A2 | 12/2008 |
| WO | 2009094670 A1 | 7/2009 |

OTHER PUBLICATIONS

State Intellectual Property Administration of the People's Republic of China, Office Action and Search Report Issued in Application No. 201610796089.6, dated Feb. 6, 2018, 8 pages.
State Intellectual Property Administration of the People's Republic of China, Office Action and Search Report Issued in Application No. 201610796082.4, dated Feb. 13, 2018, 8 pages.
European Patent Office, Supplementary European Search Report Issued in Application No. 17845507.7, dated May 28, 2020, Germany, 2 pages.

* cited by examiner

STERILIZABLE FLEXIBLE SURGICAL INSTRUMENT SYSTEM

CROSS REFERENCE TO RELATED APPLICATIONS

The present patent application is a U.S. National Phase of Chinese International Application No. PCT/CN2017/099856 entitled "STERILIZABLE FLEXIBLE SURGICAL INSTRUMENT SYSTEM" and filed on Aug. 31, 2017. Chinese International Application No. PCT/CN2017/099856 claims priority to Chinese Patent Application No. 201610796082.4 filed on Aug. 31, 2016, and Chinese Patent Application No. 201610796089.6 filed on Aug. 31, 2016. The entire contents of each of the above-identified applications are incorporated herein by reference for all purposes.

TECHNICAL FIELD

The present invention relates to a sterilizable flexible surgical instrument system, belonging to the field of medical instruments.

BACKGROUND ART

Multi-port laparoscopic minimally invasive surgery has occupied an important position in surgery because of it having small wound and rapid postoperative recovery. The existing da Vinci surgical robot of the Intuitive Surgical, Inc. assists doctors in implementing the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been further developed and have less trauma to the patient and higher postoperative outcomes. However, in the single-port laparoscopic surgery and the natural orifice transluminal non-invasive surgery, all surgical instruments including a visual illumination module and a surgical manipulator have access to the surgical site through a single channel, which is extremely stringent for the preparation of the surgical instruments. A distal structure of an existing surgical instrument is mainly of multiple rods articulated in series, and is driven by a pulling force from a wire rope, so that the surgical instrument can turn at an articulated joint. Since the wire rope has to be continuously tensioned by a pulley, this driving method can hardly lead to further miniaturization of the surgical instrument, and also further improvement of the moving performance of the instrument.

Although the Intuitive Surgical, Inc. recently introduces a da Vinci Single-Site surgical robot, in which the original rigid surgical instrument is modified into a semi-rigid surgical instrument and a pre-bent sleeve is additionally provided so as to improve the moving performance of the surgical instrument to a certain extent, it is impossible to fundamentally solve the problems faced by the traditional microsurgical instruments.

SUMMARY OF THE INVENTION

Aiming at the above problems, an object of the present invention is to provide a sterilizable flexible surgical instrument system that can be better applied to a robot system that passes through a natural orifice of human body or a single surgical incision and performs an operation.

In order to achieve the above object, the following technical solutions are used in the present invention: a sterilizable flexible surgical instrument system, comprising a flexible continuous body structure comprising a distal structural body, a middle connecting body and a proximal structural body, the distal structural body comprising at least one distal structural segment comprising a distal spacing disk, a distal fixing disk and structural backbones, the proximal structural body comprising a proximal structural segment comprising a proximal spacing disk, a proximal fixing disk and structural backbones, and the proximal end segment being linked to the distal structural segment via the middle connecting body, wherein the flexible surgical instrument system further comprises a transmission unit, the transmission unit comprises a transmission mechanism fixing plate arranged in front of the middle connecting body, a transmission mechanism for converting a rotary motion input into a linear motion output is arranged on the transmission mechanism fixing plate, an output end of the transmission mechanism is securely connected to one of a driving backbone via a adaptor, and the other end of the driving backbone passes through the proximal spacing disk and is then securely connected to the proximal fixing disk.

Preferably, the number of the proximal structural segments is equal to the number of the distal structural segments.

In one preferred embodiment, the middle connecting body comprises two channel fixing plates and a structural backbone guide channel provided between the two channel fixing plates; and the structural backbones of the distal structural segment are securely connected, in one-to-one correspondence, to or are the same as the structural backbones of the proximal structural segment, one end of each of the structural backbones is securely connected to the proximal fixing disk, passing through the proximal spacing disk, the structural backbone guide channel and the distal spacing disk in sequence, and the other end of the structural backbone is securely connected to the distal fixing disk.

In one preferred embodiment, the transmission mechanism uses a gear transmission mechanism; the gear transmission mechanism comprises a driving gear, a rack, a slider, a guide rod, a guide rod base and a steering structural backbone; the guide rod is securely connected to the transmission mechanism fixing plate or a flexible surgical instrument front end plate via the guide rod base, the slider is slidably connected to the guide rod, the slider is securely connected to the rack, the rack is securely connected to the middle of the steering structural backbone, and two ends of the steering structural backbone extend backward through the transmission mechanism fixing plate and are respectively connected to a adaptor; the rack meshes with the driving gear; and the driving gear is securely sheathed over a driving shaft, and a rear end of the driving shaft is rotatably supported on the flexible surgical instrument rear end plate located in rear of the proximal structural body and is securely connected with a male coupling.

In one preferred embodiment, the middle connecting body comprises two channel fixing plates and a structural backbone guide channel provided between the two channel fixing plates; and each of the steering structural backbones passes through the two steering structural backbone guide channels, with one end of the steering structural backbone guide channel being securely connected to the channel fixing plate, and the other end of the steering structural backbone guide channel being securely connected to the guide rod base arranged on the transmission mechanism fixing plate.

In one preferred embodiment, a guide rod is arranged between the two channel fixing plates, and the adaptor is slidably connected to the guide rod.

In one preferred embodiment, the transmission mechanism uses a pulley transmission mechanism; the pulley transmission mechanism comprises a driving pulley, a driven pulley, a cable, a slider, a guide rod, a guide rod base and a steering structural backbone; two driven pulleys are provided, and are respectively rotatably arranged on the transmission mechanism fixing plate; two ends of the cable respectively pass around the driven pulley and are then securely connected to the driving pulley; the slider is securely connected to the cable between the two driven pulleys, the slider is slidably connected to the guide rod, and the guide rod is supported on the transmission mechanism fixing plate via the guide rod base; the slider is securely connected to the middle of the steering structural backbone, and two ends of the steering structural backbone extend backward through the transmission mechanism fixing plate and are respectively connected to a linear motion mechanism; and the driving pulley is securely sheathed over a driving shaft, and a rear end of the driving shaft is rotatably supported on the flexible surgical instrument rear end plate arranged in rear of the proximal structural body and is securely connected with a male coupling.

In one preferred embodiment, the middle connecting body comprises two channel fixing plates; and the linear motion mechanism comprises a second guide rod securely connected to the two channel fixing plates and a adaptor slidably connected to the second guide rod, with a front end of the adaptor being securely connected to the steering structural backbone, and a rear end of the adaptor being securely connected to the driving backbone.

In one preferred embodiment, the middle connecting body comprises two channel fixing plates and a structural backbone guide channel provided between the two channel fixing plates; and each of the steering structural backbones passes through the two steering structural backbone guide channels, with one end of the steering structural backbone guide channel being securely connected to the channel fixing plate, and the other end of the steering structural backbone guide channel being securely connected to a support frame of the transmission mechanism fixing plate.

In one preferred embodiment, a surgical end effector is arranged at a front end of the distal structural body, a actuation wire of the surgical end effector passes through the distal structural body, the other end is connected to the end effector driving mechanism, and the surgical end effector driving mechanism implements motion control over the surgical end effector by means of physically pushing and pulling the actuation wire.

In one preferred embodiment, the surgical end effector driving mechanism comprises a threaded rod, a nut, a guide sleeve base, a guide sleeve, a push-pull rod and a male coupling; the threaded rod is rotatably connected to the flexible surgical instrument rear end plate in rear of the proximal structural body, and a rear end of the threaded rod is securely connected to the male coupling; the nut is threadedly connected to the threaded rod; a front end of the guide sleeve base is securely connected to the guide sleeve, and a rear end of the guide sleeve base is securely connected to the flexible surgical instrument rear end plate; an inner hole of the guide sleeve is a square hole in which the nut can only slide and cannot rotate; and a rear end of the push rod is securely connected to the nut, and a front end of the push rod is securely connected to the actuation wire.

In one preferred embodiment, the flexible surgical instrument system further comprises a flexible surgical instrument housing, and the transmission mechanism fixing plate, the flexible surgical instrument front end plate and the flexible surgical instrument rear end plate are all securely connected to the flexible surgical instrument housing.

In one preferred embodiment, the flexible surgical instrument system further comprises a motor driving unit, wherein the motor driving unit is connected to the flexible surgical instrument via a sterile barrier; the motor driving unit comprises a motor driving unit shell, a motor fixing plate, and a plurality of motors securely connected to the motor fixing plate, with an output shaft of each of the motors being securely connected with a second male coupling; the sterile barrier comprises a sterile barrier support plate, a sterile barrier cover, and a plurality of female couplings rotatably connected to the sterile barrier support plate, with a front end of the female coupling being connected to the male coupling, and a rear end of the female coupling being connected to the second male coupling; and a sterile membrane is securely connected to the sterile barrier cover.

In one preferred embodiment, a front end of the motor fixing plate is provided with a first connecting pin seat, and a rear end of the sterile barrier support plate is provided with a second connecting pin seat, the first connecting pin seat being connected to the second connecting pin seat via a pin hole.

In one preferred embodiment, the flexible surgical instrument system further comprises a motor driving unit, wherein the motor driving unit is connected to the flexible surgical instrument via a sterile barrier; the motor driving unit comprises a motor driving unit shell, a motor fixing plate, and a second motor securely connected to the motor fixing plate, the motor fixing plate being rotatably connected to the motor driving unit shell, an inner wall of the motor driving unit shell being securely connected with an inner ring gear, an output shaft of the second motor being securely connected with a gear, and the gear meshing with the inner ring gear.

In one preferred embodiment, the flexible surgical instrument system further comprises a motor driving unit shell and a linear module, wherein the motor driving unit shell is directly or indirectly connected to the flexible surgical instrument housing; and the linear module comprises a bracket body, a third motor securely connected to the bracket body, and a linear feed mechanism securely connected to an output shaft of the third motor, with an output end of the linear feed mechanism being securely connected to the motor driving unit shell, and the third motor driving the motor driving unit shell via the linear feed mechanism to drive the motor driving unit, the sterile barrier and the flexible surgical instrument to perform a linear motion.

In one preferred embodiment, the linear feed mechanism comprises a lead screw rotatably connected to the bracket body, the lead screw is sheathed with a second slider which is threadedly fitted with the lead screw, the bracket body is provided with a linear sliding groove, and the second slider is slidably arranged in the linear sliding groove; and the output shaft of the third motor is securely connected to the lead screw via a coupling.

The present invention has the following advantages due to utilizing the above technical solutions: 1. In the present invention, a flexible continuous body structure comprising a proximal structural body, a middle connecting body and a distal structural body is used as the main body, and cooperates with a transmission unit, wherein the distal structural body is linked to the proximal structural body via the middle connecting body, the transmission unit is linked to the proximal structural body, and when the motor driving unit drives the proximal structural body to turn in any direction, the distal structural body correspondingly turns in the opposite direction, so as to implement the turning motion in any direction of a flexible surgical arm formed of the distal structural body and an envelope. 2. In the present invention, in the proximal structural body, the middle connecting body and the distal structural body, a redundant arrangement of structural backbones (the number of the structural backbones is more than three) is used, which can improve the safety, reliability and load capacity of the flexible surgical instrument system. 3. In the present invention, the flexible surgical instrument is connected to the motor driving unit via a sterile barrier with a sterile membrane, thereby effectively isolating an unsterilized part from a sterilized part of the system to ensure the practicability of clinical operations. 4. In the present invention, multiple gear transmission mechanisms are provided in the flexible surgical instrument, the gear transmission mechanism can convert a rotary motion input of the driving shaft into a linear motion output, a strand of multiple steering structural backbones with smaller stiffness is fixedly connected inside one of the gear transmission mechanisms, the strand of steering structural backbones can implement turning in a large angle space and transmit the linear motion output, two ends of the steering structural backbone are respectively fixedly connected to one of the ends of different driving backbones with a greater stiffness, and the other ends of the driving backbones are all fixedly connected inside the proximal structural body and finally cooperatively drive the proximal structural body by means of the multiple gear transmission mechanisms to turn in any direction in a small space. 5. In the present invention, a front end of the distal structural body is provided with a surgical end effector, a actuation wire of the surgical end effector passes through the distal structural body, and the other end is connected to the surgical end effector driving mechanism at the middle connecting body, thereby implementing motion control over the surgical end effector. 6. In the present invention, an inner wall of the motor driving unit shell is securely provided with an inner ring gear, the motor fixing plate is provided with a motor to drive the parts other than the shell and the inner ring gear to rotate, and therefore the motor can be used to drive the parts other than the motor driving unit shell and the inner ring gear to rotate as a whole so as to adjust the roll angle of the surgical end effector. 7. The present invention is further provided with a linear module which is connected to the shell and can drive the shell to perform a linear motion, and therefore the flexible surgical arm also has a linear feed degree of freedom.

The present invention can be applied to the single-port endoscopic surgery, and can also be applied to the natural orifice transluminal non-invasive surgery.

DETAILED DESCRIPTION OF EMBODIMENTS

The present invention is to be described in detail below in conjunction with the accompanying drawings and embodiments.

Figure 1:
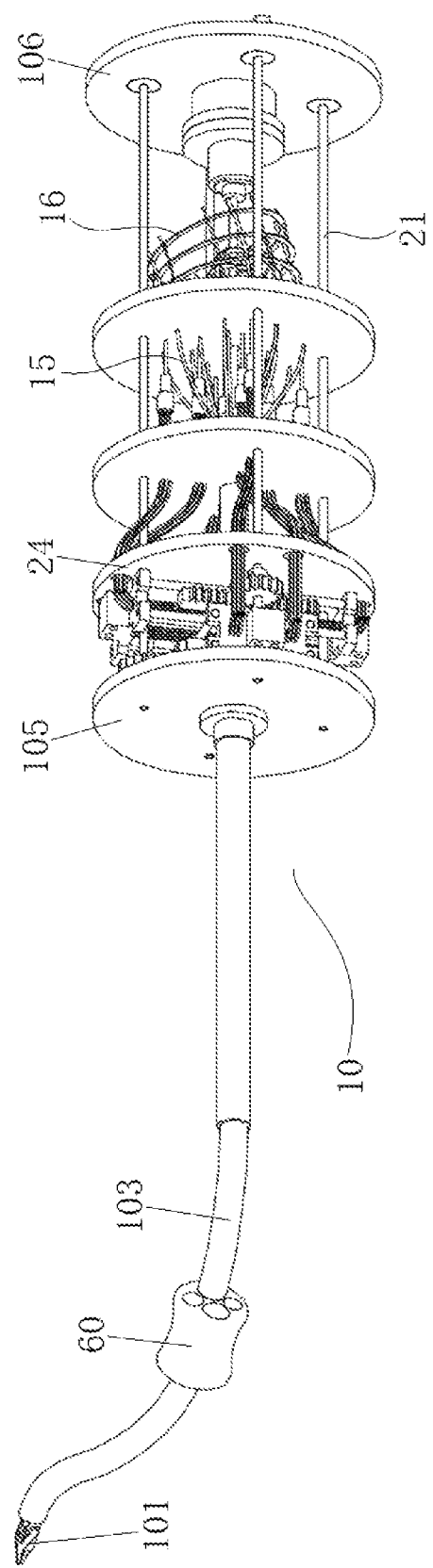
FIG. 1 is an overall structural schematic diagram according to the present invention.
Figure 2:
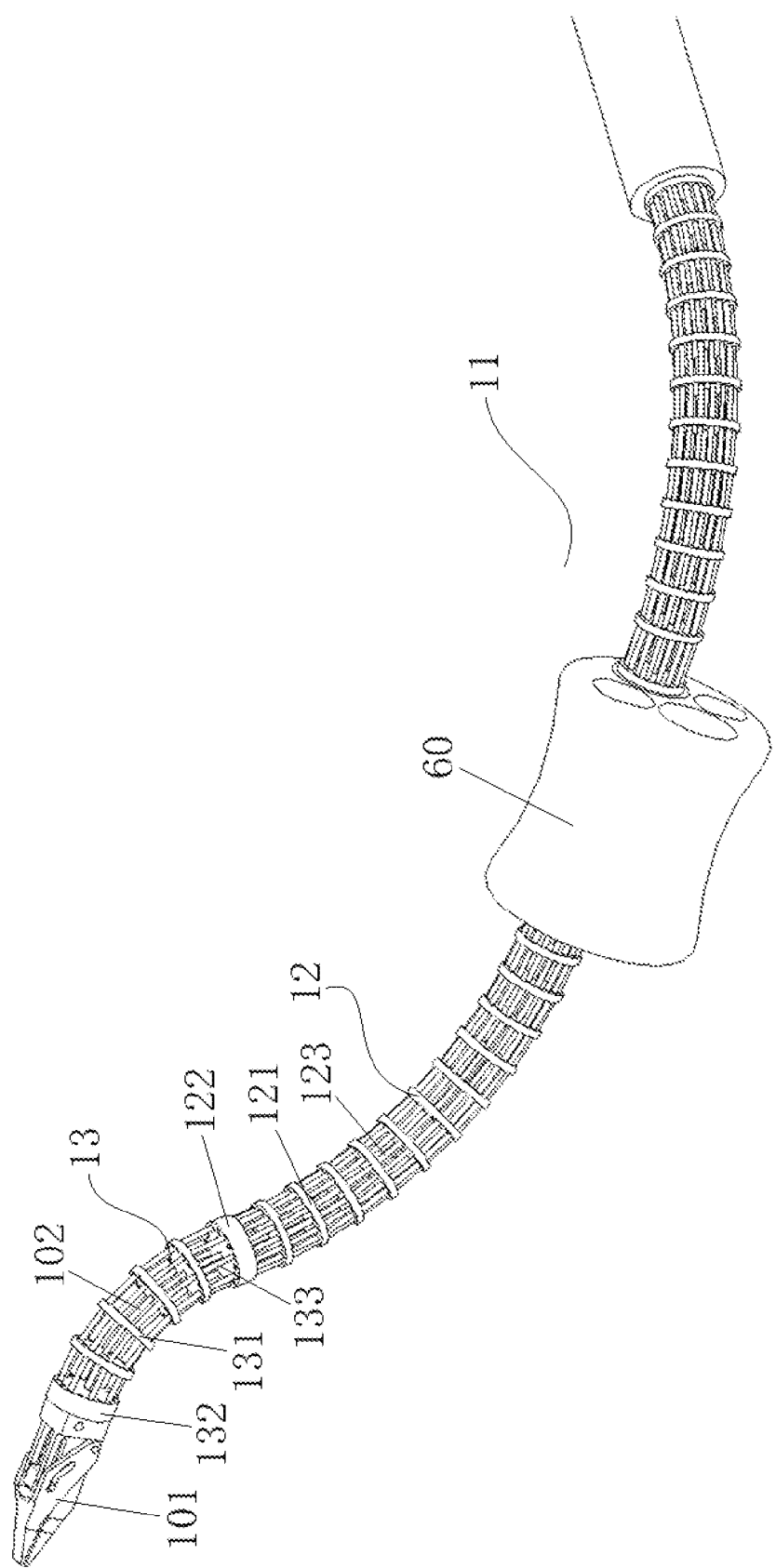
FIG. 2 is a structural schematic diagram of a distal structural body according to the present invention.
Figure 3:
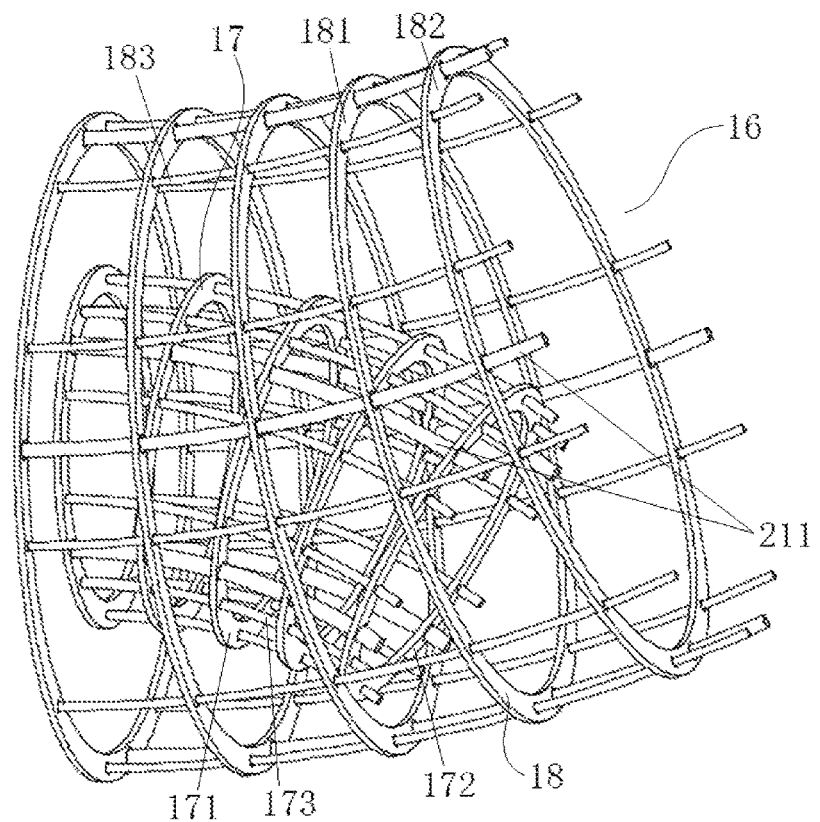
FIG. 3 is a structural schematic diagram of a proximal structural body according to the present invention.
Figure 5:
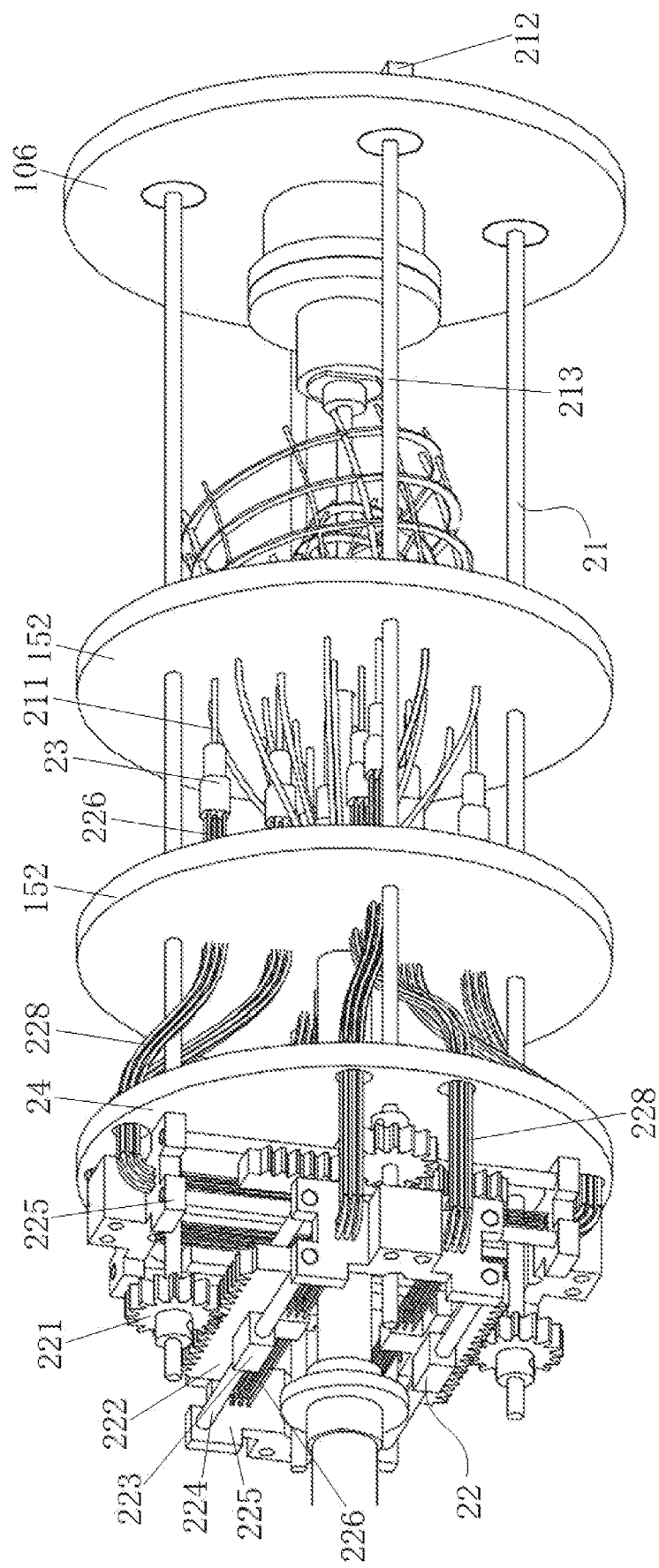
FIG. 5 is a structural schematic diagram of a transmission unit according to the present invention, with a gear transmission mechanism being used.

As shown in FIG. 1, the present invention comprises a flexible surgical instrument 10, and the flexible surgical instrument 10 comprises a flexible continuous body structure and a transmission unit 21, the flexible continuous body structure being composed of a distal structural body 11 (as shown in FIG. 2), a proximal structural body 16 (as shown in FIG. 3) and a middle connecting body 15 (as shown in FIG. 5). The distal structural body 11 is linked to the proximal structural body 16 via the middle connecting body 15; and the transmission unit 21 is linked to the proximal structural body 16, and when the transmission unit 21 drives the proximal structural body 16 to turn in any direction, the distal structural body 11 correspondingly turns in the opposite direction.

As shown in FIG. 2, the distal structural body 11 comprises a first distal structural segment 12 and a second distal structural segment 13, wherein the first distal structural segment 12 comprises first distal spacing disks 121, a first distal fixing disk 122 and first segment structural backbones 123; and the second distal structural segment 13 comprises second distal spacing disks 131, a second distal fixing disk 132 and second segment structural backbones 133. The first distal spacing disks 121 and the second distal spacing disks 131 are respectively distributed at intervals in the first distal structural segment 12 and the second distal structural segment 13, in order to prevent the first segment structural backbones 123 and the second segment structural backbones 133 from being destabilized when being pushed.

As shown in FIG. 3, the proximal structural body 16 comprises a first proximal structural segment 17 and a second proximal structural segment 18, wherein the first proximal structural segment 17 comprises first proximal spacing disks 171, a first proximal fixing disk 172 and first segment structural backbones 173; and the second proximal structural segment 18 comprises second proximal spacing disks 181, a second proximal fixing disk 182, and second segment structural backbones 183, wherein the first proximal spacing disks 171 and the second proximal spacing disks 181 are respectively distributed at intervals in the first proximal structural segment 17 and the second proximal structural segment 18, in order to prevent the first segment structural backbones 173 and the second segment structural backbones 183 from being destabilized when being pushed. The first segment structural backbones 173 on the first proximal structural segment 17 are securely connected, in one-to-one correspondence, to or are the same as the first segment structural backbones 123 on the first distal structural segment 12; and the second segment structural backbones 183 on the second proximal structural segment 18 are securely connected, in one-to-one correspondence, to or are the same as the second segment structural backbones 133 on the second distal structural segment 13. For each of the proximal structural segments 17, 18 and each of the distal structural segments 12, 13, the number of structural backbones is three or more.

Figure 4:
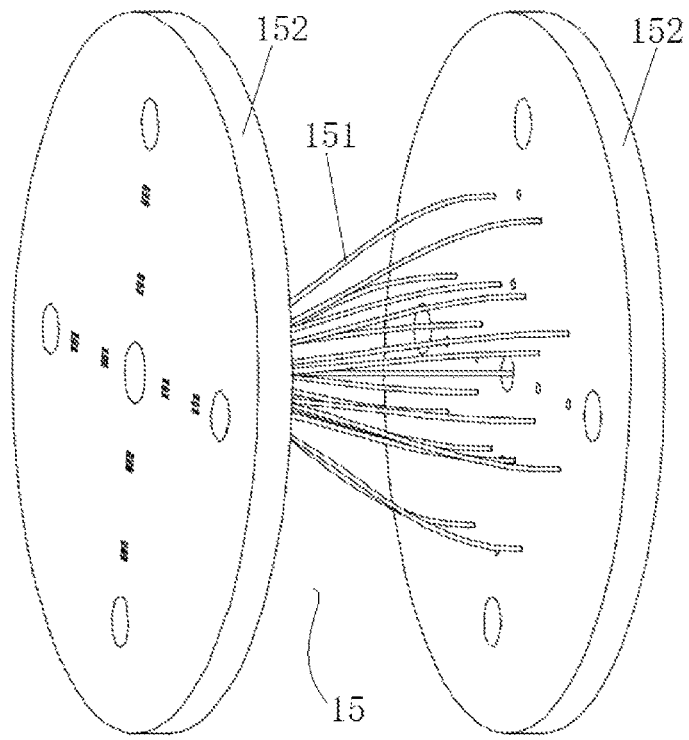
FIG. 4 is a structural schematic diagram of a middle connecting body according to the present invention.

As shown in FIG. 4, the middle connecting body 15 comprises two channel fixing plates 152 and a structural backbone guide channel 151 fixedly connected between the two channel fixing plates 152. One end of the first segment structural backbone 173 (123) is securely connected to the first proximal fixing disk 172, and the other end passes through the first proximal spacing disks 171, the structural backbone guide channel 151 and the first distal spacing disks 121 in sequence and is then securely connected to the first distal fixing disk 122. One end of the second segment structural backbone 183 (133) is securely connected to the second proximal fixing disk 182, and the other end passes through the second proximal spacing disks 181, the structural backbone guide channel 151, the first distal structural segment 12 and the second distal spacing disks 131 in sequence and is then securely connected to the second distal fixing disk 132. The structural backbone guide channel 151 functions to maintain the shape of the structural backbone under a pushing or pulling force.

The number of the distal structural segments comprised in the distal structural body 11 and the number of the proximal structural segments comprised in the proximal structural body 16 may also be one or more than two, but the number of the proximal structural segments must be consistent with the number of the distal structural segments. In addition, when the number of the distal structural segments comprised in the distal structural body 11 is two or more, the distal structural segments are connected in series, that is, the second segment structural backbone passes through the first distal fixing disk and the first distal spacing disks (and can also pass through the first segment structural backbone if the first segment structural backbone is of a tubular structure); and when the number of the proximal structural segments comprised in the proximal structural body 16 is two or more, series connection, independent arrangement or nested arrangement (as shown in FIG. 3), etc. may be applied between the structural segments.

As shown in FIGS. 1 and 5-7, the transmission unit 21 comprises a transmission mechanism fixing plate 24 arranged in front of the middle connecting body 15, and a gear transmission mechanism 22 arranged between the transmission mechanism fixing plate 24 and the flexible surgical instrument front end plate 105 or a pulley transmission mechanism 27 arranged on the transmission mechanism fixing plate 24, both the gear transmission mechanism 22 and the pulley transmission mechanism 27 being used for converting a rotary motion input into a linear motion output. When the gear transmission mechanism 22 is used, an output end of the gear transmission mechanism 22 is respectively securely connected to one ends of two driving backbones 211 via two adaptors 23; and when the pulley transmission mechanism 27 is used, an output end of the pulley transmission mechanism 27 is respectively securely connected to one end of two driving backbones 211 via two linear motion mechanisms 28 arranged between the two channel fixing plates 152. The other ends of the two driving backbones 211 respectively pass through the first proximal spacing disk 171 and are then securely connected to the first proximal fixing disk 172, or pass through the second proximal spacing disk 181 and are then securely connected to the second proximal fixing disk 182. Thus, by means of one gear transmission mechanism 22 or pulley transmission mechanism 27, a pair of driving backbones 211 can be pushed or pulled cooperatively so as to implement turning of the first proximal structural segment 17 or the second proximal structural segment 18. In this embodiment, the number of driving backbones 211 is eight, four of which are securely connected to the first proximal fixing disk 172, and the other four are securely connected to the second proximal fixing disk 182. Since the gear transmission mechanisms 22 or pulley transmission mechanisms 27 can cooperatively push or pull a pair of driving backbones 211, four gear transmission mechanisms 22 or four pulley transmission mechanisms 27 are provided in this embodiment, in which two of the gear transmission mechanisms 22 or the pulley transmission mechanisms 27 are used to drive the first proximal structural segment 17 to perform a turning motion in any direction, and when the first proximal structural segment 17 turns in a certain direction, the first distal structural segment 12 will turn in the opposite direction in a certain proportional relationship (determined by the distribution radius of the first segment structural backbone 173 and the first segment structural backbone 123 together); and the other two gear transmission mechanisms 22 or pulley transmission mechanisms 27 are used to drive the second proximal structural segment 18 to perform a turning motion in any direction, and when the second proximal structural segment 18 turns in a certain direction, the second distal structural segment 13 will turn in the opposite direction in a certain proportional relationship (determined by the distribution radius of the second segment structural backbone 183 and the second segment structural backbone 133 together).

The gear transmission mechanism 22 and the pulley transmission mechanism 27 will be respectively described below:

As shown in FIG. 5, the gear transmission mechanism 22 comprises a driving gear 221, a rack 222, a slider 223, a guide rod 224, a guide rod base 225 and a steering structural backbone 226, wherein the guide rod 224 is securely connected to the transmission mechanism fixing plate 24 or the flexible surgical instrument front end plate 105 via the guide rod base 225, the slider 223 is slidably connected to the guide rod 224, the slider 223 is securely connected to the rack 222, the rack 222 is securely connected to the middle of a bundle of steering structural backbones 226, and two ends of the bundle of steering structural backbones 226 extend backward through the transmission mechanism fixing plate 24 and are then connected to one of the driving backbones 211 via one of the adaptors 23, respectively. The rack 222 meshes with the driving gear 221, the driving gear 221 is securely sheathed over the driving shaft 213, the rear end of the driving shaft 213 passes through the transmission mechanism fixing plate 24, the channel fixing plate 152, and the flexible surgical instrument rear end plate 106 arranged in rear of the proximal structural body 16 in sequence, and is securely connected to the male coupling 212, and the driving shaft 213 is rotatably connected to the flexible surgical instrument rear end plate 106.

Further, a plurality of guide rods are provided between two channel fixing plates 152, and the adaptor 23 is slidably connected to the guide rod, so as to ensure that the adaptor 23 always performs a linear motion, preventing the adaptor 23 from turning over when the driving backbone 211 is pushed or pulled.

Further, each of the steering structural backbones 226 passes through the two steering structural backbone guide channels 228, with one end of the steering structural backbone guide channel being securely connected to the channel fixing plate 152, and the other end being securely connected to the guide rod base 225, and the steering structural backbone guide channel 228 functions to keep the shape of the steering structural backbone 226 unchanged under a pushing or pulling force.

Figure 6:
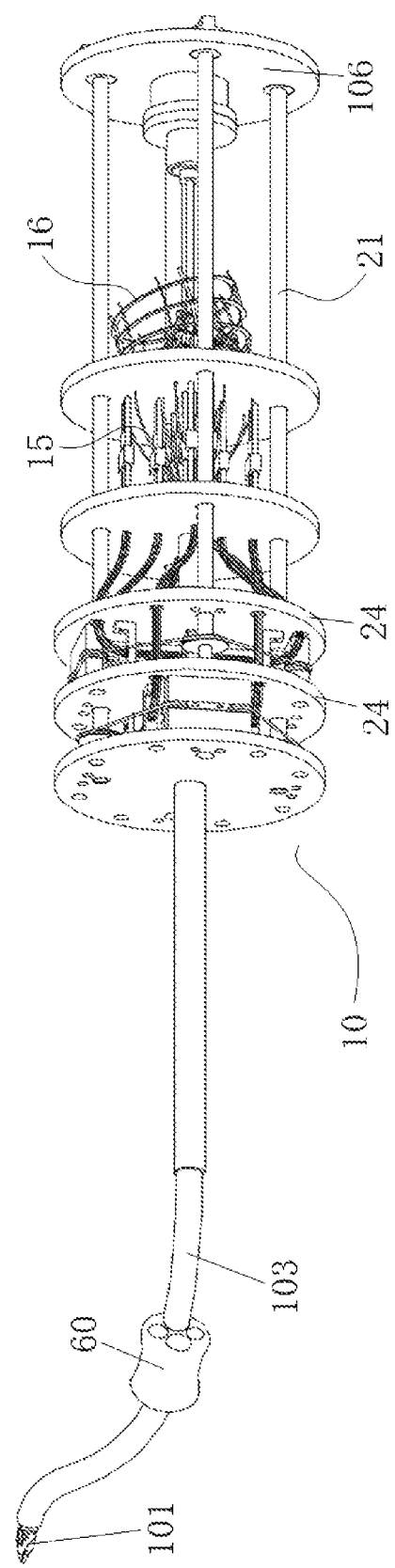
FIG. 6 is an overall structural schematic diagram according to the present invention, with a pulley transmission mechanism being used.
Figure 7:
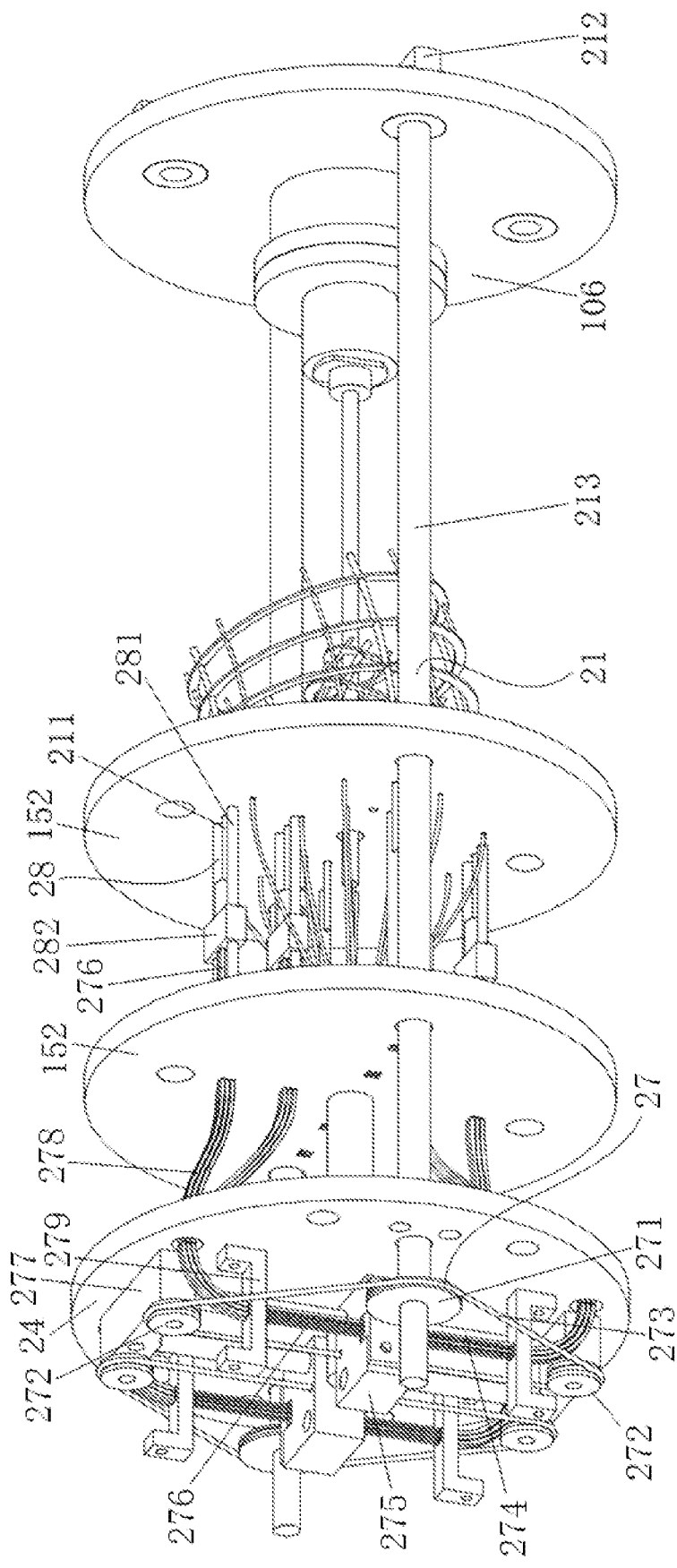
FIG. 7 is a structural schematic diagram of a transmission unit according to the present invention, with a pulley transmission mechanism being used.
Figure 8:
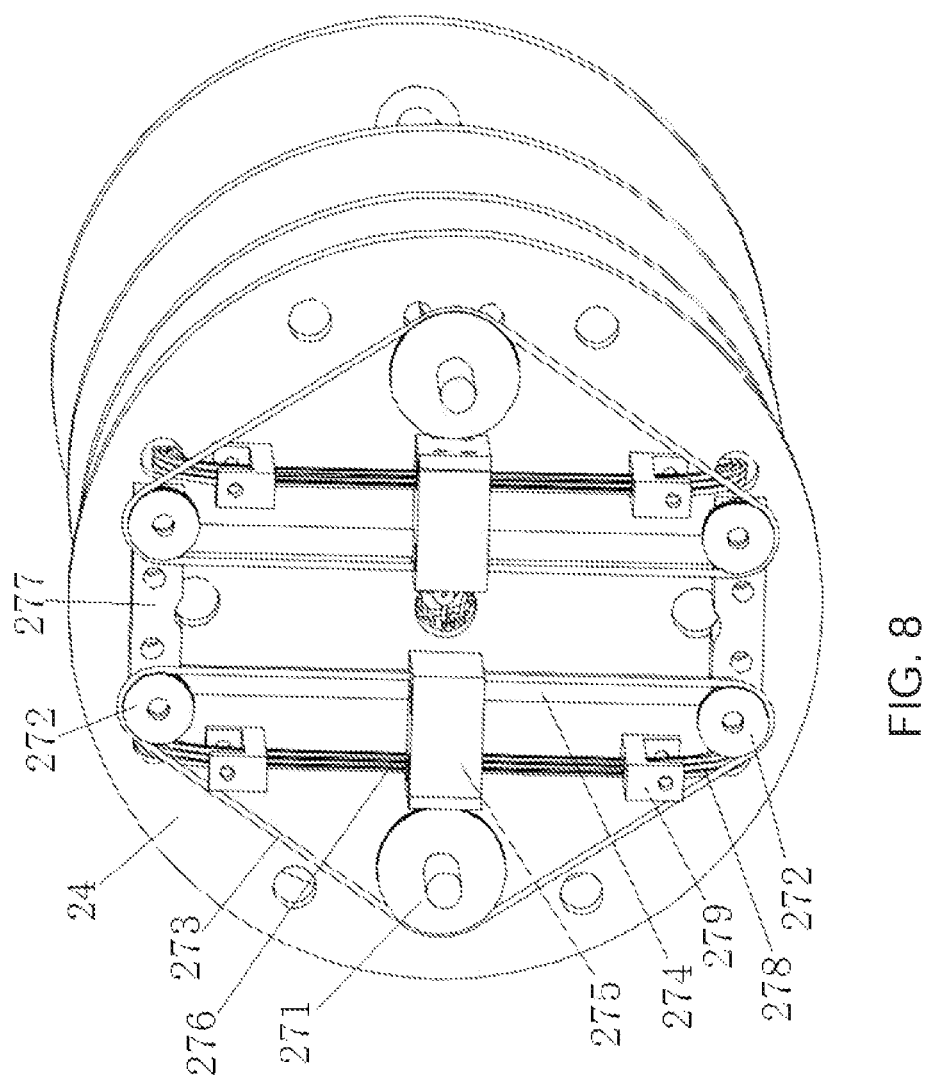
FIG. 8 is a structural schematic diagram of a pulley transmission mechanism according to the present invention.

As shown in FIGS. 6 to 8, the pulley transmission mechanism 27 comprises a driving pulley 271, a driven pulley 272, a cable 273, a slider 275, a guide rod 274, a guide rod base 277 and a steering structural backbone 276, wherein two driven pulleys 272 are provided and respectively rotatably arranged on the transmission mechanism fixing plate 24, two ends of the cable 273 respectively pass around a driven pulley 272 and are then securely connected to the driving pulley 271, the driving pulley 271 is securely sheathed over the driving shaft 213, the rear end of the driving shaft 213 pass through the transmission mechanism fixing plate 24, the channel fixing plate 152, and the flexible surgical instrument rear end plate 106 arranged in rear of the proximal structural body 16 in sequence, and is securely connected to the male coupling 212, and the driving shaft 213 is rotatably connected to the flexible surgical instrument rear end plate 106. A slider 275 is securely connected to the cable 273 between two driven pulleys 272, the slider 275 is slidably connected to the guide rod 274, and the guide rod 274 is fixedly supported on the transmission mechanism fixing plate 24 via the guide rod base 277. The slider 275 is securely connected to the middle of a bundle of steering structural backbones 276, and two ends of the bundle of steering structural backbones 276 extend backward through the transmission mechanism fixing plate 24 and are respectively connected to the linear motion mechanism 28. The linear motion mechanism 28 comprises a guide rod 281 securely connected between the two channel fixing plates 152 and a adaptor 282 slidably connected to the guide rod 281, with a front end of the adaptor 282 being securely connected to the steering structural backbone 276, and a rear end of the adaptor being securely connected to the driving backbone 211.

Further, each of the steering structural backbones 276 passes through the two steering structural backbone guide channels 278, with one end of the steering structural backbone guide channel being securely connected to the channel fixing plate 152, and the other end of the steering structural backbone being securely connected to a support frame 279 fixedly arranged at a front side of the transmission mechanism fixing plate 24, and the steering structural backbone guide channel 278 functions to keep the shape of the steering structural backbone 276 unchanged under a pushing or pulling force.

Figure 9:
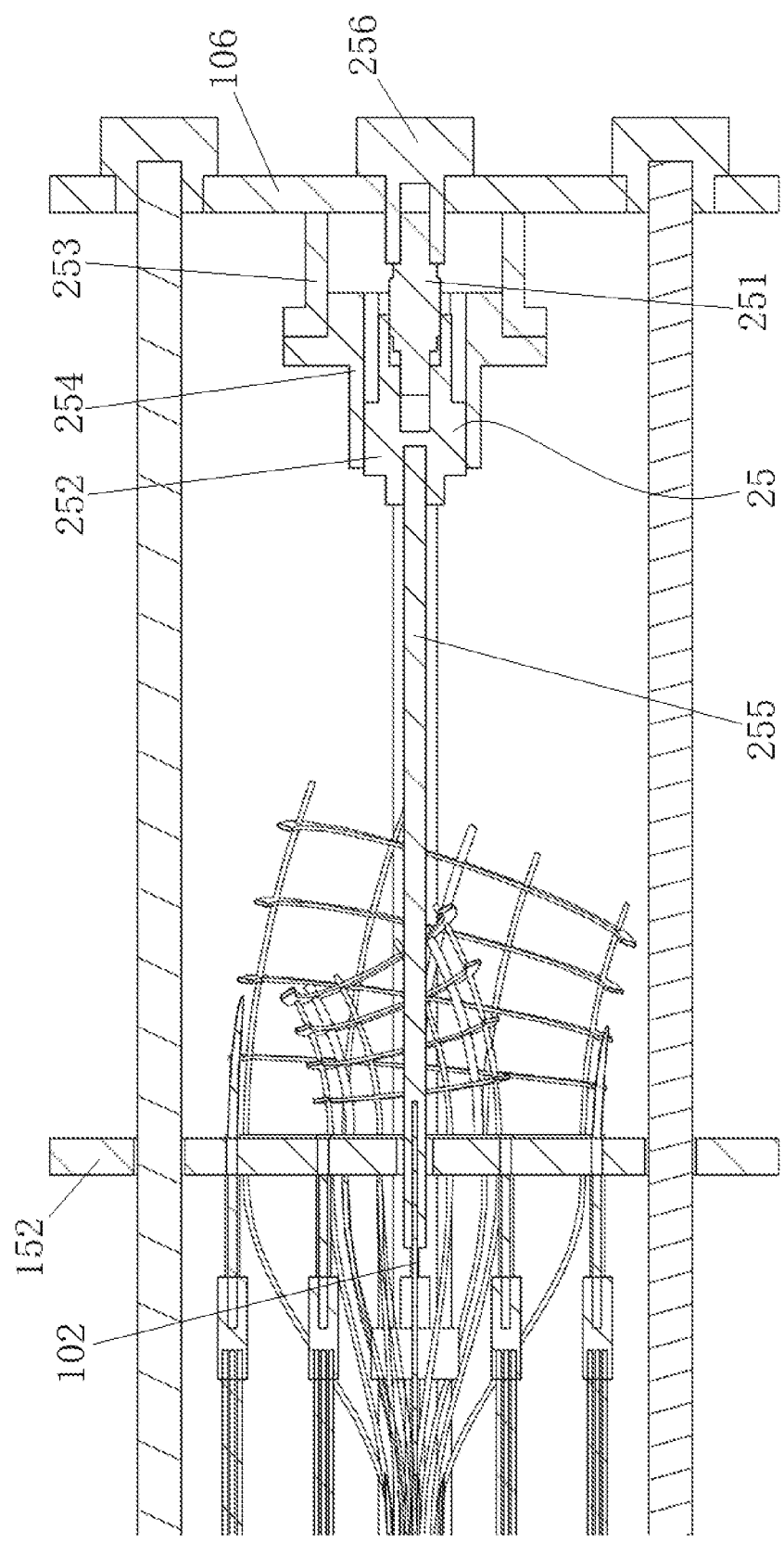
FIG. 9 is a structural schematic diagram of a surgical end effector driving mechanism according to the present invention.

In the above embodiment, the front end of the distal structural body 11 is provided with a surgical end effector 101 (as shown in FIG. 2), a actuation wire 102 of the surgical end effector 101 passes through the distal structural body 11, and the other end is connected to the surgical end effector driving mechanism 25. The surgical end effector driving mechanism 25 implements control over the surgical end effector 101 (e.g., surgical forceps) by means of physically pushing or pulling the actuation wire 102. The actuation wire 102 may also transfer various forms of energy, such as electrical energy and high-frequency vibrations, to achieve specific surgical functions of the surgical end effector 101. As shown in FIG. 9, the surgical end effector driving mechanism 25 comprises a threaded rod 251, a nut 252, a guide sleeve base 253, a guide sleeve 254, a push-pull rod 255 and a male coupling 256, wherein the threaded rod 251 is rotatably connected to the center of the flexible surgical instrument rear end plate 106, a rear end of the threaded rod is securely connected to the male coupling 256, and the nut 252 is threadedly connected to the threaded rod 251; a front end of the guide sleeve base 253 is securely connected to the guide sleeve 254, and a rear end of the guide sleeve base is securely connected to the flexible surgical instrument rear end plate 106; an inner hole of the guide sleeve 254 is a square hole and forms a restriction on the nut 252, so that the nut 252 can only slide in the inner hole of the guide sleeve 254 and cannot rotate; and a rear end of the push-pull rod 255 is securely connected to the nut 252, and a front end of the push-pull rod is securely connected to the actuation wire 102.

Figure 10:
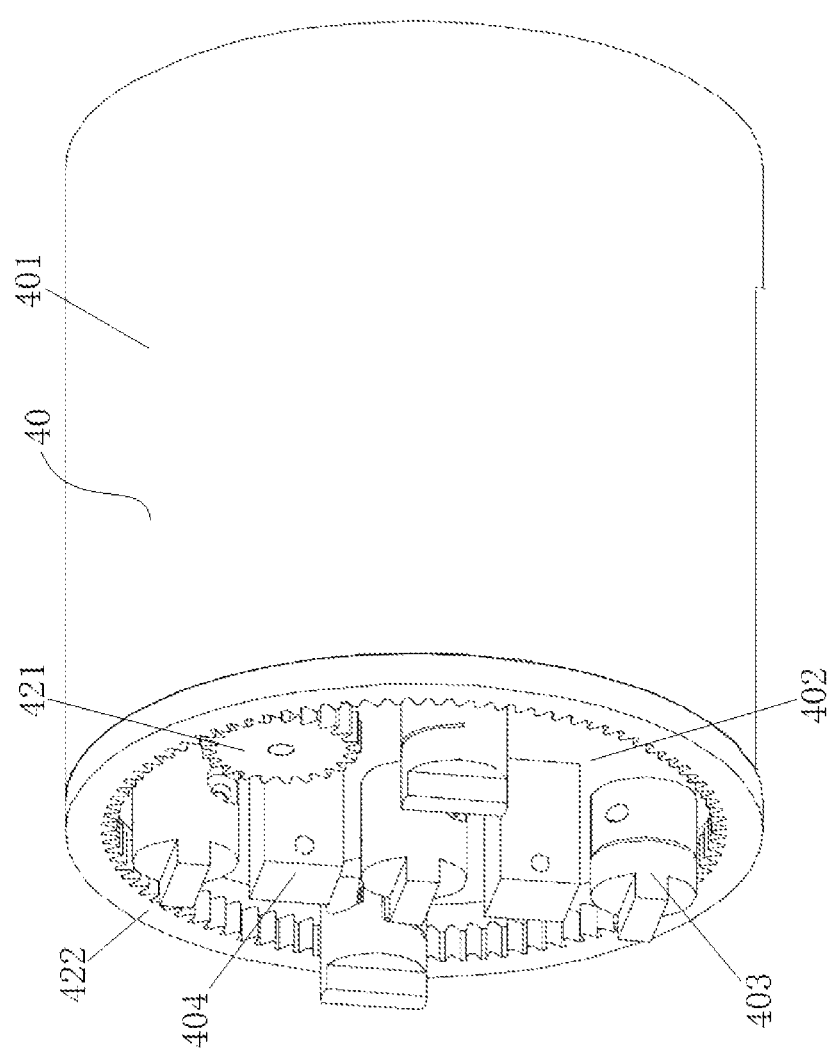
FIG. 10 is a structural schematic diagram of a motor driving unit according to the present invention.
Figure 11:
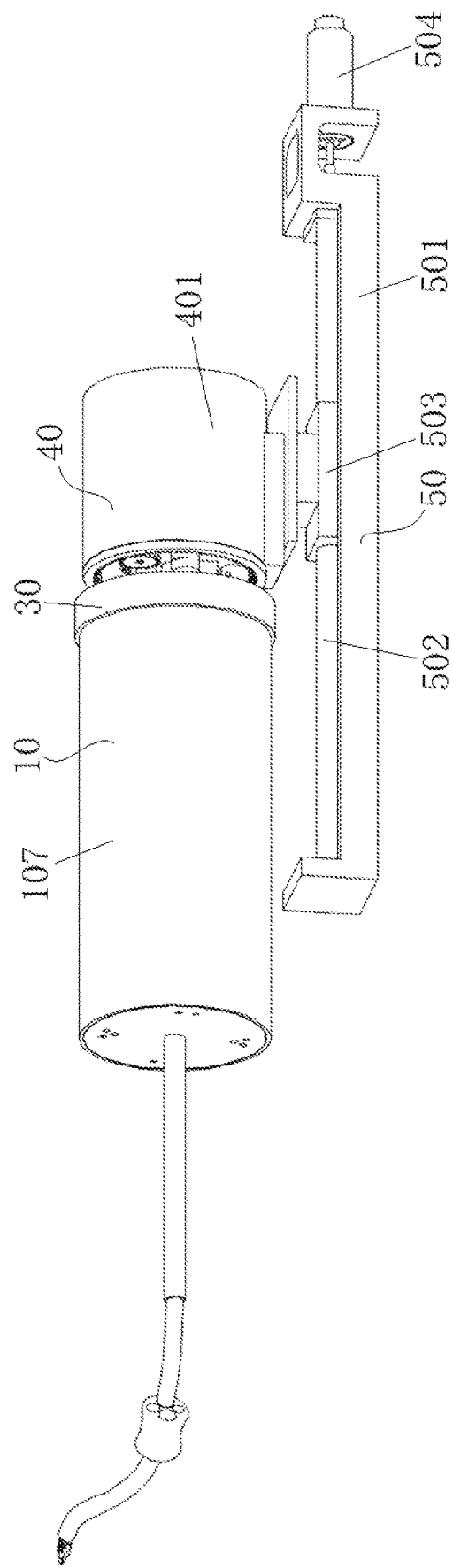
FIG. 11 is a structural schematic diagram according to the present invention, with a flexible surgical instrument housing, a sterile barrier and a linear module being mounted.
Figure 12:
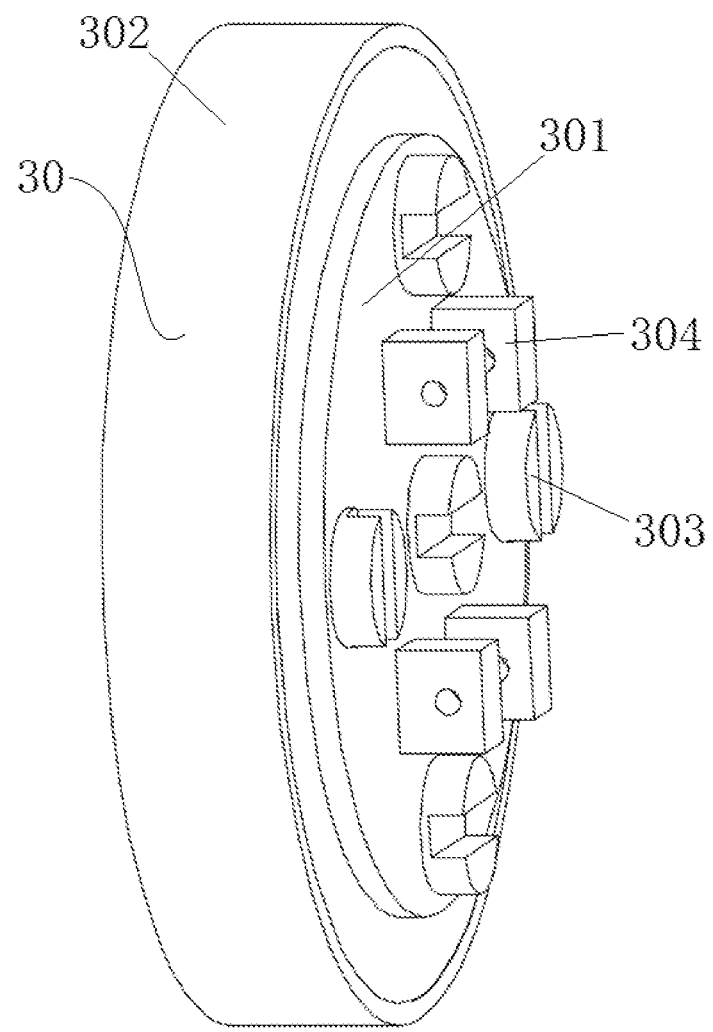
FIG. 12 is a structural schematic diagram of a sterile barrier according to the present invention.

In the above embodiment, as shown in FIGS. 10 and 11, the present invention further comprises a motor driving unit 40, and the motor driving unit 40 is connected to the flexible surgical instrument 10 via the sterile barrier 30. The flexible surgical instrument 10 further comprises a flexible surgical instrument housing 107, and the channel fixing plate 152, the transmission mechanism fixing plate 24 and the flexible surgical instrument rear end plate 106 are all securely connected to the flexible surgical instrument housing 107. The motor driving unit 40 comprises a motor driving unit shell 401, a motor fixing plate 402, and a plurality of first motors (not shown in the figure) securely connected to the motor fixing plate 402, with an output shaft of each of the first motors being securely connected to one of the male couplings 403. As shown in FIG. 12, the sterile barrier 30 comprises a sterile barrier support plate 301, a sterile barrier cover 302 and a plurality of female couplings 303 rotatably connected to the sterile barrier support plate 301, with a rear end of the female coupling 303 being connected to the male coupling 403, and a front end of the female coupling being connected to the male coupling 212 or the male coupling 256. A front side of the motor fixing plate 402 is provided with a connecting pin seat 404, and a rear side of the sterile barrier support plate 301 is correspondingly provided with a connecting pin seat 304, the connecting pin seat 404 being quickly connected to the connecting pin seat 304 via a pin hole; and the sterile barrier cover 302 is detachably connected to the surgical instrument housing 107. A sterile membrane (not shown in the figure) is securely connected on the sterile barrier cover 302 to isolate the sterilizable parts (such as the flexible surgical instrument 10 and other parts in front of the sterile barrier 30) from the unsterilized parts (such as the motor driving unit 40 and other parts in rear of the sterile barrier), in order to ensure the clinical practicability of surgery.

In the above embodiment, it is a rotatable connection provided between the motor fixing plate 402 and the motor driving unit shell 401, an inner wall of the motor driving unit shell 401 is securely connected with an inner ring gear 422, the motor fixing plate 402 is also securely connected with a second motor (not shown in the figure), an output shaft of the second motor is securely connected with a gear 421, and the gear 421 meshes with an inner ring gear 422. When the output shaft of the second motor rotates, the gear 421 is driven to rotate, and the gear 421 circumferentially travels along the inner ring gear 422, so as to drive all structures, other than the motor driving unit shell 401 and the inner ring gear 422 to rotate around the axis of the inner ring gear 422, thereby implementing the rotation of the flexible surgical instrument 10 as a whole and achieving control over the roll angle of the distal structural body 101 and the surgical end effector 30.

In the above embodiment, as shown in FIG. 11, the present invention further comprises a linear module 50 (the linear module 50 being also separated from the sterilized part via the sterile membrane 230), which comprises a bracket body 501 with a sliding groove, a lead screw 502 is rotatably provided on the bracket body 501, the lead screw 502 is sheathed with a slider 503 which is threadedly fitted with the lead screw 502 and is slidably provided in the sliding groove, one end of the bracket body 501 is provided with a motor 504, and an output shaft of the motor 504 is securely connected to the lead screw 502 via a coupling. The motor driving unit housing 401 is securely connected to the slider 503. When the output shaft of the motor 504 rotates, the slider 503 drives the motor driving unit housing 401 to perform linear movement along the sliding groove, so as to implement the feed motion of the flexible surgical instrument 10.

Figure 13:
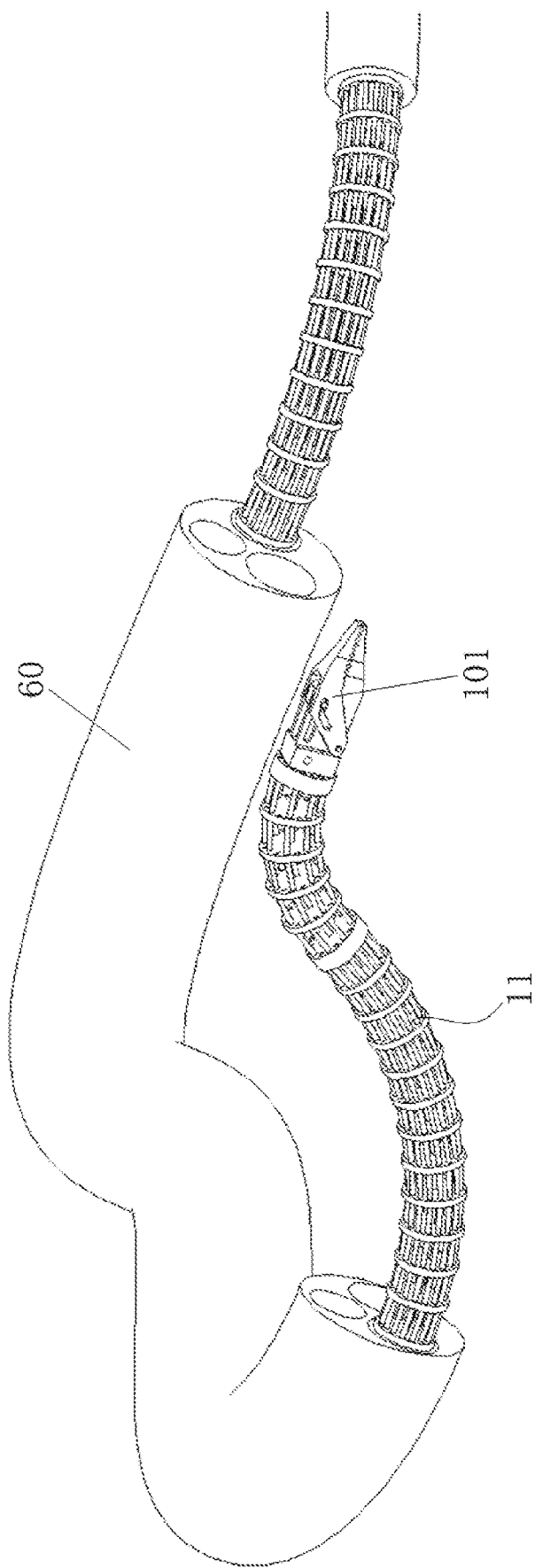
FIG. 13 is a structural schematic diagram of a distal structural body according to the present invention, with a flexible sheath being used.

In the above embodiment, as shown in FIG. 1, an envelope 103 is provided over the outside of the distal structural body 11 and functions to improve the smoothness of the distal structural body 11 entering a natural orifice or a surgical incision in the human body. A sheath 60 (as shown in FIG. 2) may also be provided over the outside of the envelope 103. In an application, the sheath 60 is fixed at a single incision in the abdominal cavity, and the distal structural body 11, together with the envelope 103 and the surgical end effector 101, can freely pass through a through hole in the sheath 60 for the passage of the surgical instrument and access to the surgical site. As shown in FIG. 13, in another application, the sheath 60 may also be a flexible sheath that can more easily extend into various natural orifices of the human body and adaptively change shape as the shape of the orifices, one end of the flexible sheath is fixed at the entrance of the orifice, and the distal structural body 11, together with the envelope 103 and the surgical end effector 101, can freely pass through a through hole in the flexible sheath for the passage of the surgical instrument and access to the surgical site.

The present invention has been illustrated only by means of the above embodiment, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument, comprising:
a distal structural body comprising at least one distal structural segment each comprising a distal fixing disk and distal structural backbones;
a proximal structural body comprising at least one proximal structural segment each comprising a proximal fixing disk, proximal structural backbones, at least one first driving backbone, and at least one second driving backbone, the distal structural backbones being securely connected in one-to-one correspondence to or the same as corresponding proximal structural backbones; and
a transmission unit comprising a transmission mechanism operable to convert a rotary motion into a linear motion,
the transmission mechanism comprising:
at least one steering backbone to transmit the linear motion, and the at least one steering backbone is operable to cooperatively push-pull the at least one first driving backbone and the at least one second driving backbone to turn the proximal structural segment;
wherein a proximal end of the at least one first driving backbone and a proximal end of the at least one second driving backbone are securely connected to the proximal fixing disk;
wherein a first end of the at least one steering backbone is connected to a distal end of the at least one first driving backbone, and a second end of the at least one steering backbone is connected to a distal end of the at least one second driving backbone.

2. The flexible surgical instrument of claim 1, wherein the at least one steering backbone each comprises a bundle of steering structural backbones.

3. The flexible surgical instrument of claim 1, wherein the transmission mechanism comprises at least one steering structural backbone guide channel, the at least one steering backbone passing through the at least one steering structural backbone guide channel.

4. The flexible surgical instrument of claim 3, further comprising a middle connecting body comprising:
a first channel fixing plate near the distal structural body; and
a second channel fixing plate near the proximal structural body, and
structural backbone guide channels are provided between the first channel fixing plate and the second channel fixing plate,
the distal structural backbones pass through the structural backbone guide channels and distal ends of the distal structural backbones are securely connected to the distal fixing disk.

5. The flexible surgical instrument of claim 4, wherein the transmission mechanism comprises:
a transmission mechanism fixing plate provided at distal end of the middle connecting body;
the at least one steering structural backbone guide channel comprising at least one first steering structural backbone guide channel and at least one second steering structural backbone guide channel;
the at least one first steering structural backbone guide channel is connected to the transmission mechanism fixing plate and the first channel fixing plate;
the at least one second steering structural backbone guide channel is connected to the transmission mechanism fixing plate and the first channel fixing plate, and
the at least one steering backbone passes through the at least one first steering structural backbone guide channel and the at least one second steering structural backbone guide channel.

6. The flexible surgical instrument of claim 1, wherein proximal ends of the proximal structural backbones are securely connected to the proximal fixing disk, and distal ends of the distal structural backbones are securely connected to the distal fixing disk.

7. The flexible surgical instrument of claim 1, wherein the proximal structural segment further comprises a proximal spacing disk, the proximal structural backbones passing through the proximal spacing disk; and the distal structural segment further comprises a distal spacing disk, the distal structural backbones passing through the distal spacing disk.

8. The flexible surgical instrument of claim 1, wherein the transmission mechanism comprises a gear transmission mechanism connected to the at least one steering backbone and operable to convert the rotary motion into the linear motion.

9. The flexible surgical instrument of claim 8, wherein the gear transmission mechanism comprises:
   a driving gear to receive the rotary motion; and
   a rack meshing with the driving gear and connected to the at least one steering backbone.

10. The flexible surgical instrument of claim 1, wherein the transmission mechanism comprises a pulley transmission mechanism connected to the at least one steering backbone and operable to convert a rotary motion into the linear motion.

11. The flexible surgical instrument of claim 10, wherein the pulley transmission mechanism comprises:
   a cable;
   a slider connected to the cable and on the at least one steering backbone;
   a driving pulley to receive the rotary motion;
   at least one driven pulley rotated by the driving pulley through the cable.

12. The flexible surgical instrument of claim 1, further comprising:
   a surgical end effector provided at a distal end of the distal structural body; and
   an actuation wire of the surgical end effector passing through the distal structural body, the surgical end effector actuation wire comprising a proximal end securely connected to a surgical end effector driving mechanism and a distal end securely connected to the surgical end effector.

13. The flexible surgical instrument of claim 12, wherein the surgical end effector driving mechanism comprises:
   a threaded rod;
   a nut in threaded connection with the threaded rod; and
   a push-pull rod comprising a proximal end securely connected to the nut and a distal end securely connected to the surgical end effector actuation wire.

14. A flexible surgical instrument system, comprising:
   the flexible surgical instrument of claim 1; and
   a motor driving unit to input rotational motion to the transmission mechanism.

15. The flexible surgical instrument system of claim 14, further comprising:
   a flexible surgical instrument housing; and
   a sterile barrier provided between the flexible surgical instrument housing and the motor driving unit.

16. The flexible surgical instrument system of claim 15, wherein the motor driving unit comprises:
   a motor driving unit shell;
   a motor fixing plate; and
   a plurality of first motors securely connected to the motor fixing plate, and
   the sterile barrier comprises:
   a sterile barrier support plate securely connected to the motor fixing plate; and
   a sterile barrier cover detachably connected to the flexible surgical instrument housing.

17. The flexible surgical instrument system of claim 14, wherein the motor driving unit comprises:
   a motor driving unit shell;
   a motor fixing plate being rotatably connected to the motor driving unit shell; and
   a motor securely connected to the motor fixing plate;
   an internal ring gear being securely connected to an internal wall of a motor assembly housing; and
   a gear being engaged with the internal ring gear, and the gear being securely connected to a shaft of the motor.

18. The flexible surgical instrument system of claim 14, further comprising:
   a linear module to drive the flexible surgical instrument and the motor driving unit to perform a linear motion.

* * * * *